(12) United States Patent
Jackovitch

(10) Patent No.: US 6,929,614 B1
(45) Date of Patent: Aug. 16, 2005

(54) FLEXION CONTROL ANKLE JOINT HINGE

(76) Inventor: Timothy D. Jackovitch, 902 Eagles View Rd., Hayesville, NC (US) 28904

( * ) Notice: Subject to any disclaimer, the term of this patent is extended or adjusted under 35 U.S.C. 154(b) by 23 days.

(21) Appl. No.: 10/807,860

(22) Filed: Mar. 24, 2004

Related U.S. Application Data

(60) Provisional application No. 60/457,270, filed on Mar. 25, 2003.

(51) Int. Cl.$^7$ .............................................. A61F 5/00
(52) U.S. Cl. ........................................ 602/16; 602/27
(58) Field of Search ............................. 602/16, 5, 28, 602/29, 65

(56) References Cited

U.S. PATENT DOCUMENTS

| | | | |
|---|---|---|---|
| 292,800 A | 2/1884 | Furrer | |
| 3,982,278 A | 9/1976 | May | |
| 4,320,747 A * | 3/1982 | Daniell, Jr. | 602/16 |
| 4,499,613 A | 2/1985 | Yarrow | |
| 4,605,417 A | 8/1986 | Fleischauer | |
| 4,614,181 A * | 9/1986 | Karlsson | 602/16 |
| 4,728,336 A | 3/1988 | Cooper | |
| 5,112,356 A | 5/1992 | Harris et al. | |
| 5,156,630 A | 10/1992 | Rappoport et al. | |
| 5,242,379 A * | 9/1993 | Harris et al. | 602/27 |
| 5,244,455 A * | 9/1993 | Swicegood et al. | 602/16 |
| 5,443,527 A | 8/1995 | Wilson | |
| 5,482,513 A | 1/1996 | Wilson | |
| 5,542,774 A * | 8/1996 | Hoy | 403/116 |
| 5,545,234 A | 8/1996 | Collier, Jr. | |
| 5,611,773 A * | 3/1997 | Nash et al. | 602/16 |
| 5,695,526 A | 12/1997 | Wilson | |
| 5,728,175 A | 3/1998 | Rincoe | |
| 5,746,773 A | 5/1998 | Littig | |
| 5,766,264 A | 6/1998 | Lundt | |
| 5,851,194 A * | 12/1998 | Fratrick | 602/28 |
| 5,954,677 A * | 9/1999 | Albrecht et al. | 602/16 |
| 5,997,493 A * | 12/1999 | Young | 602/16 |
| 6,033,440 A | 3/2000 | Schall et al. | |
| 6,231,618 B1 | 5/2001 | Schall et al. | |
| D448,484 S * | 9/2001 | Bradshaw | D24/155 |
| 6,375,632 B1 * | 4/2002 | Albrecht et al. | 602/16 |
| 6,635,024 B2 * | 10/2003 | Hatton et al. | 602/16 |
| D489,135 S * | 4/2004 | Slautterback et al. | D24/192 |
| 6,752,774 B2 * | 6/2004 | Townsend et al. | 602/16 |
| 6,824,523 B2 * | 11/2004 | Carlson | 602/16 |
| 2004/0127825 A1 * | 7/2004 | Castillo et al. | 602/5 |

\* cited by examiner

*Primary Examiner*—Henry Bennett
*Assistant Examiner*—Dinnatia Doster Greene
(74) *Attorney, Agent, or Firm*—Hinkle & O'Bradovich, LLC

(57) ABSTRACT

A joint hinge, an ankle brace and a method of installing the joint hinge in an ankle brace. The joint hinge typically allows a patient or practitioner to set a range limiting system that includes threaded rods that are easy to screw in and out as the patient's range of motion changes. In a typical embodiment, a proximal plate rotates about a pin with respect to a distal plate. The pin is generally aligned with the patient's ankle. The range limiting system's rods screw toward and away from a portion of the proximal plate, thereby limiting the range of the proximal, and therefore, the distal plates. The proximal plate is connected to the proximal portion of the ankle brace and the distal plate is connected to the distal portion of the ankle brace.

9 Claims, 3 Drawing Sheets

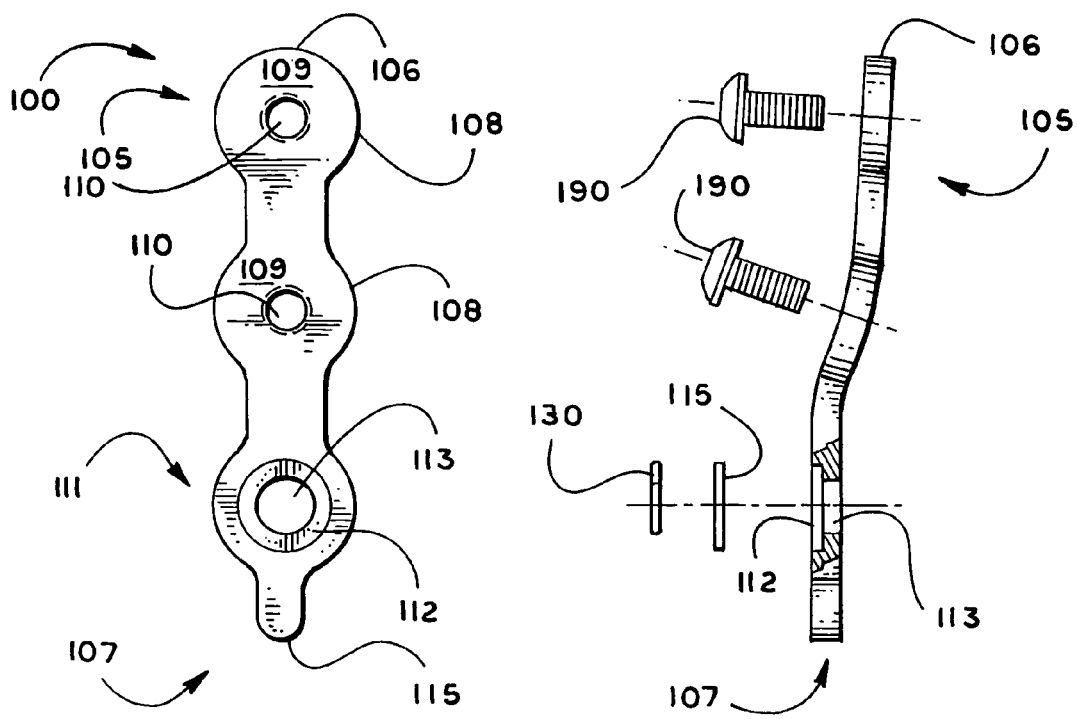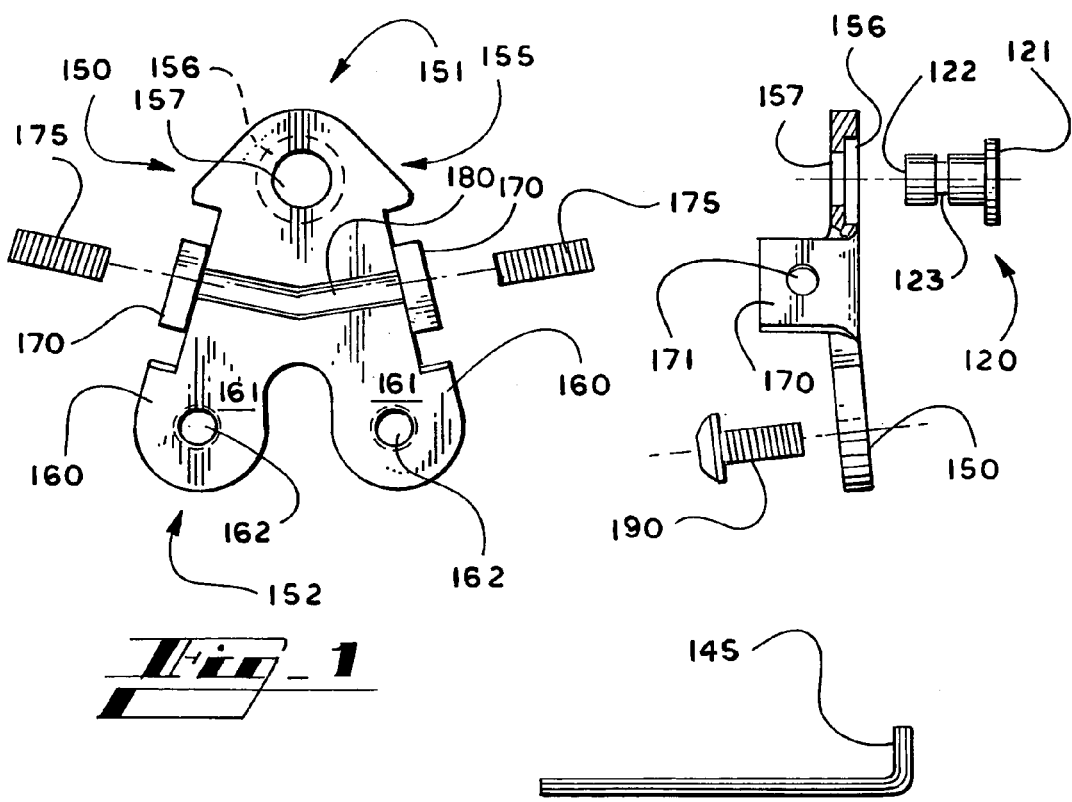
Fig_1

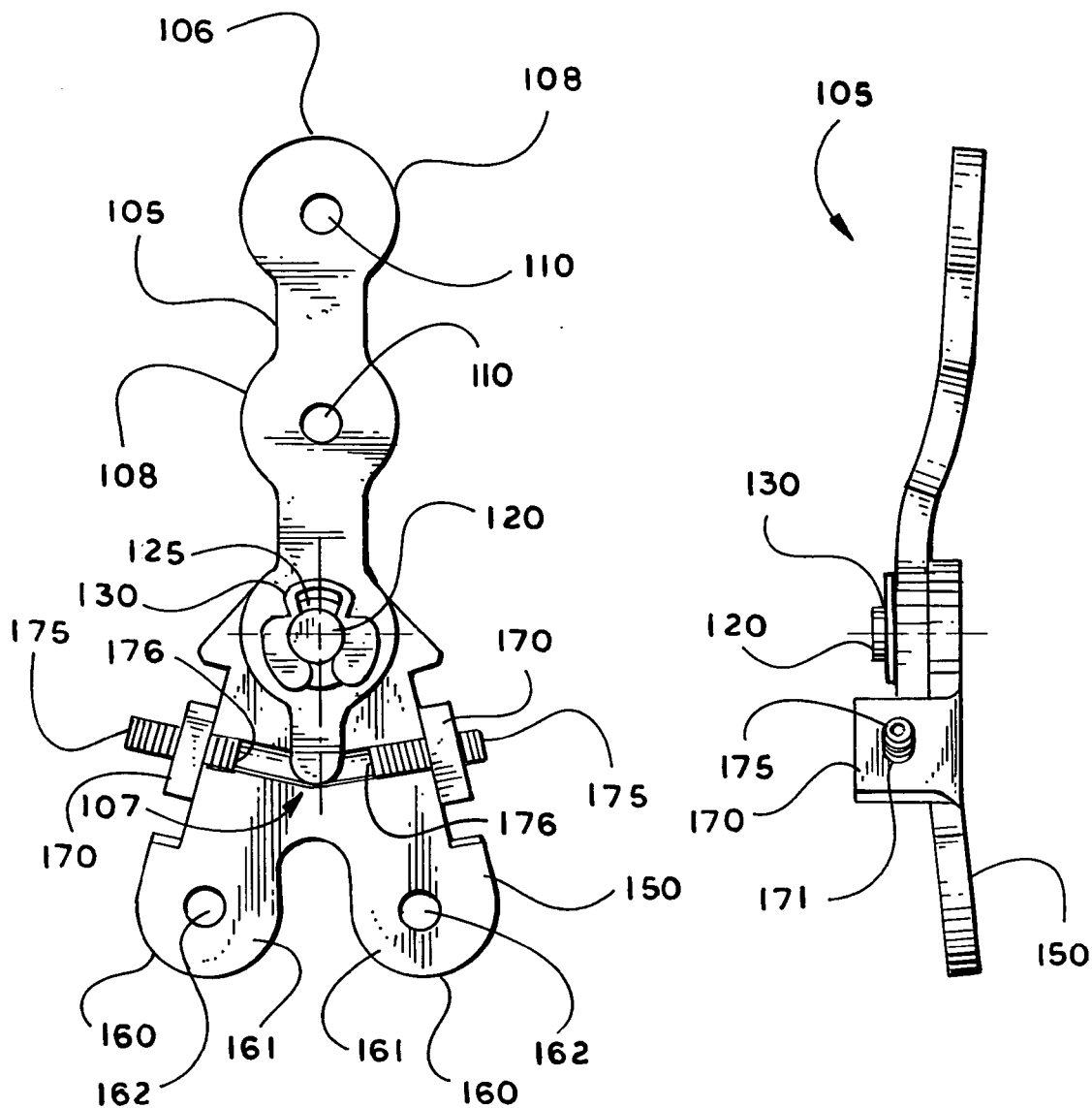
Fig_2

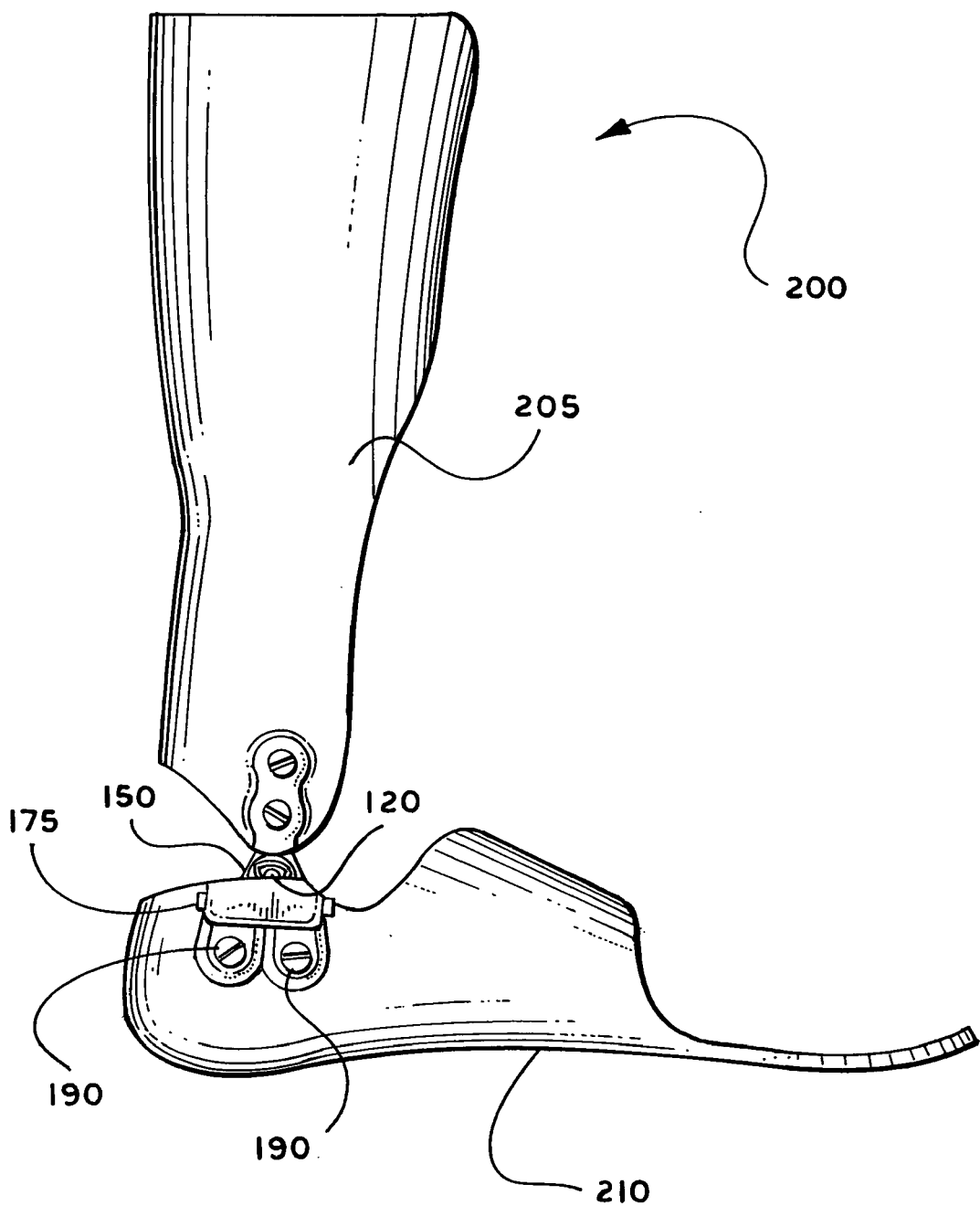
Fig_3

FLEXION CONTROL ANKLE JOINT HINGE

Priority based on Provisional Application Ser. No. 60/457,270, filed Mar. 25, 2003, and entitled "Flexion Control Ankle Joint Hinge", is claimed.

BACKGROUND

I. Field of the Invention

The present invention relates generally to the field of orthotic devices and more particularly to ankle foot orthoses with a flexion control ankle hinge apparatus, system and method.

II. Description of the Related Art

Present leg braces provide control for plantar flexion and/or porsiflexion. Present flexion control devices typically include proximal set-screws that set the flexion in either direction at set increments. These devices typically are bulky and difficult to fit in the patient's shoe, and are difficult to adjust due to the fact that they include definite settings that can only be adjusted in increments. Other devices require separate pieces, such as range of motion keys, which must be inserted and replaced as the patient's range of motion increases or decreases.

SUMMARY

In general, the invention features a joint hinge and a leg brace having the joint hinge that allow a patient or practitioner to set an anterior-posterior range limiting system that include rods that are threaded and easy to screw in and out as the patient's range of motion changes. In a typical embodiment, a proximal plate rotates about a pin with respect to a distal plate. The pin is generally aligned with the patient's ankle axis. The range limiting system's rods screw toward and away from a portion of the proximal plate, thereby limiting the range of the proximal, and therefore, the distal plates. The proximal plate is connected to the proximal portion of the ankle brace and the distal plate is connected to the distal portion of the ankle brace.

In general, in one aspect, the invention features a flexion joint apparatus incorporated into a leg brace, including a proximal plate having an upper end and a lower end, a distal plate connected to the proximal plate and an anterior-posterior range limiting system, including a tongue connected to the second end of the proximal plate, and two tongue-stops connected to the distal plate at a generally perpendicular orientation, wherein each of the tongue-stops includes a threaded hole through which a threaded rod is connected to the tongue-stops in threaded engagement.

In one implementation, the apparatus further includes a pin connecting the distal and proximal plates in pivotal arrangement, a washer in mechanical engagement with the pin and a clip connected to the pin, the clip preventing the distal and proximal plates from disassembling.

In another implementation, the pin includes a generally cylindrical base, a cylindrical stem connected generally perpendicular to a center point of the cylindrical base and a continuous trench on a circumference of the stem adjacent one end of the stem opposite the cylindrical base.

In another implementation, the clip is connected to the trench on the stem of the pin.

In another implementation, the apparatus further includes a conduit located on the distal plate and partially surrounding each of the threaded rods.

In yet another implementation, the apparatus includes ankle brace connection points located on the proximal and distal plates, each ankle brace connection point, comprising a generally circular-shaped base surrounding a hole.

In still another implementation, the proximal plate further comprises a distal plate connection point having a generally cylindrical depression with a hole located generally in the middle of the depression.

In another implementation, the distal plate further comprises a proximal plate connection point having a generally cylindrical depression with a hole located generally in the middle of the depression.

In another aspect, the invention features a flexion joint apparatus, including a proximal plate having a tongue protruding from an end of the proximal plate, a distal plate having a protrusion connected generally perpendicular to each side of the distal plate, wherein the tongue of the proximal plate overlaps a portion of the distal plate and travels a path along the distal plate, each end of the path terminating in a respective one of the protrusions and a pin connected through the proximal and distal plates.

In still another aspect, the invention features a flexion joint apparatus, including a body including a proximal plate having a tongue and distal plate having a protrusion on either side of the distal plate and means for limiting the relative motion of the proximal plate with respect to the distal plate.

In still another aspect, the invention features an ankle brace system, including an ankle brace, a flexion joint apparatus connected to the ankle brace, the flexion control apparatus including, a proximal plate having an upper end and a lower end, a distal plate connected to the proximal plate and a range limiting system, having a tongue connected to the second end of the proximal plate, and two tongue-stops connected to the distal plate at a generally perpendicular orientation, wherein each of the tongue-stops includes a threaded hole through which a threaded rod is connected to the tongue-stops in threaded engagement.

In another aspect, the invention features a method of installing an ankle joint in a leg brace, including pouring the cast, modifying the cast, locating the ankle axis, square the ankle joint with the external squaring fixture, vacuum forming plastic on the cast, cooling the plastic and removing the brace.

One advantage of the invention is that the range of motion of the joint hinge and therefore a leg brace can be easily set by the patient or practitioner.

Another advantage of the invention is that a range limiting system allows the patient or practitioner to set a continuum of settings to meet the individual needs of a patient.

Another advantage of the invention is that the threaded rods in the range limiting system are set in the anterior and posterior directions.

Other objects, advantages and capabilities of the invention will become apparent from the following description taken in conjunction with the accompanying drawings showing the preferred embodiment of the invention.

BRIEF DESCRIPTION OF THE DRAWINGS

FIG. 1 illustrates respective front and side views of the constituent components of an embodiment of a flexion control ankle hinge apparatus;

FIG. 2 illustrates a front and side view of an embodiment of a flexion control ankle joint hinge; and FIG. 3 illustrates an embodiment of an ankle brace having an embodiment of flexion control ankle joint hinge apparatus connected to the brace.

DETAILED DESCRIPTION

Referring to the drawings wherein like reference numerals designate corresponding parts throughout the several figures, reference is made first to FIG. 1 that illustrates respective front and side views of the constituent components of an embodiment of a flexion control ankle hinge apparatus 100. The apparatus 100 typically includes a proximal plate 105 and a distal plate 150. Additional components include a pin 120 having a generally cylindrical base 121 and a generally cylindrical stem 122 having a diameter narrower than the diameter of the base, a generally circular washer 125 and a clip 130. The stem 122 of the pin 120 includes a trench 123 along a portion of the perimeter of the stem 122. In general, as discussed further in the description below, the clip 120 fits into the trench 123 to secure the proximal and distal plates 105, 150.

The proximal plate 105, which is comprised of an upper and lower end 106, 107, typically includes one or more brace connection points 108 that are used in conjunction with an ankle brace as described further below with respect to a flexion control ankle joint hinge system. One of the brace connection points 108 is typically located at the upper end 106 of the proximal plate 105. Another brace connection point 108 is typically positioned between the upper and lower ends 106, 107. The brace connection points 108 are typically wider than the overall width of the proximal plate 105 and have a generally circular-shaped base 109. A hole 110 is also located approximately in the center of each base 109 of the connection points 108. The proximal plate 105 further includes a distal plate connection point 111 positioned adjacent the lower end 107. The distal plate connection point 111 includes a generally cylindrical depression 112 with a hole 113 in the middle of the depression 112. As described further below, the depression 112 receives the washer 125 when the component pieces are assembled.

The proximal plate 105 also includes a tongue 115 connected to the lower end 107 of the proximal plate 105. The tongue 115 is a protrusion and is generally narrower than the overall width of the proximal plate 105. The tongue 115 is part of the overall range limiting system that is discussed further in the description below.

As shown in the side view of the proximal plate 105, the upper and lower ends 106, 107 of the proximal plate 105 are offset from each other due to a gradual curvature of the proximal plate 105. A portion of the lower end 107 is elevated slightly with respect to the upper end 106. A bend, causing the overall curvature, in the proximal plate 105 typically achieves this elevation differential. As described further below, when the distal plate 150 and proximal plate 105 are connected, this elevation differential results in the upper end 106 of the proximal plate 105 and the distal plate 150 being oriented in a similar positional plane.

The distal plate 150 generally includes an upper end 151 and a lower end 152. The upper end 151 of the distal plate 150 includes a proximal plate connection point 155. The proximal plate connection point 155 generally includes a smooth outer curvature 158 that generally follows the resulting path of curvature of the proximal plate 105 with respect to the distal plate 150 when the two are attached and move with respect to one another. The proximal plate connection point 155 includes a generally cylindrical depression 156, as shown in phantom, with a hole 157 in the middle on the rear side of the distal plate 150. The generally cylindrical depression 156 typically receives the cylindrical base 121 of the pin 120 when the proximal and distal plates 105, 150 are attached. The stem 122 of the pin 120 fits through both of the holes 113, 157 of the distal and proximal plate connection points 111, 151 as further discussed in the description below.

The lower end 152 of the distal plate 150 typically includes two brace connection points 160. Similar to the brace connection points 108 of the proximal plate 105, the brace connection points 160 of the distal plate 150 have a generally circular-shaped base 161. A hole 162 is also located approximately in the center of each base 161 of each brace connection point 160.

The distal plate 150 further includes a tongue-stop 170 on each side of the distal plate 150, located generally between the upper and lower ends 151, 152. The tongue-stops 170 are typically a small plate protrusion generally perpendicular to the overall surface of the distal plate 150, although other angles are anticipated. Each of the tongue-stops 170 includes threaded holes 171 through which the threaded rod 175 is typically connected in threaded engagement. The tongue-stops 170 are part of the overall range limiting system that is discussed further in the description below. A conduit 180 is located on a portion of the distal plate 150 adjacent the tongue-stops 175. The conduit 180 is generally oriented to receive the threaded rods 175 as the rods 175 transverse through the holes 171 on the tongue stops 170 as they are screwed into and out of the tongue stops 170. Since the threaded rods 175 are not typically oriented in opposition, the conduit 180 it typically bends, thereby generally changing the direction of the conduit 180, at an approximate center location of the distal plate 150. In other embodiments, the threaded rods 175 can be oriented in opposition and, therefore, the conduit 180 can be in a continuous straight line.

As shown in the side view of the distal plate 150, the upper and lower ends 151, 152 of the distal plate 150 are offset from each other due to a gradual curvature of the distal plate 150. A portion of the lower end 152 is curved slightly with respect to the upper end 151. As described further below, when the distal plate 150 and proximal plate 105 are connected, this elevation differential results in the upper end 106 of the proximal plate 105 and the lower end 152 of the distal plate 150 being oriented in a similar positional plane.

The apparatus 100 further includes several screws 190 that can be used to connect the apparatus 100 to an ankle brace to form an overall brace system. In general, the screws 190 can be used to engage the holes 110, 162 in the brace connection points 111, 160 of the proximal and distal plates 105, 150 respectively. The holes 110, 162 can include threads so that the screws 190 can be in threaded engagement with the screws 190. The apparatus 100 can further include an external adjustment instrument 195, such as a hex wrench which can be used to adjust the threaded rods 175 within the holes 171 of the tongue-stops 170 as part of the overall range limiting system. The apparatus 100, the screws 190 and the adjustment instrument 195 can be included together as an overall ankle brace kit.

FIG. 2 illustrates a front view and a side view of an embodiment of a flexion control ankle joint hinge apparatus 100. The apparatus 100 generally includes the proximal plate 105 and a distal plate 150 that are pivotally connected to each other. The connected proximal and distal plates 105, 150 make up a main body in which the proximal and distal plates 105, 150 pivot with respect to each other. The pivotal connection includes the hole 113, 157 in each of the proximal and distal connection points 111, 155 through which the stem 122 of the pin 120 is set. As described above, the cylindrical base 121 of the pin 120 is set in the depression 156 of the proximal plate connection point 155 on the distal plate 150. With both the proximal and distal plates 105, 150 connected in this way, the stem 122 of the pin 120 protrudes slightly through the hole 113 of the distal plate connection point 111 on the proximal plate 105. The washer 125 is set in the depression 112 of the distal plate connection point 111 on the lower end 107 of the proximal plate 105. The stem 122 of the pin 120 also protrudes from the washer 125. The small trench 123 that runs continuously around the circumference of the stem 122 adjacent the tip of the stem 122 opposite the base 121. The clip 130 is set into the trench 123 and locks into place.

With the component pieces assembled in this manner, the distal and proximal plates 105, 150 remain connected to each other. The plates 105, 150 can pivot with respect to each other about the pin 120 with the aid of the washer 125. The clip 130 prevents the component pieces from coming disassembled.

The side view illustrates the relative position of the proximal and distal plates 105, 150 with respect to each other showing certain dimensional features. Specifically, as mentioned above, there is an elevation differential between the upper and lower ends 106, 107 of the proximal plate 105. When the proximal and distal plates 105, 150 are assembled, the upper end 106 of the proximal plate 105 is generally in the same plane as the lower end 152 the distal plate 150 and the lower end 107 of the proximal plate 105 is located in a plane generally parallel to overall orientation of the distal plate 150. Furthermore, as described above the lower end 152 of the distal plate 150 is slightly curved. The dimensional features as just described have significance with respect to the flexion control ankle joint hinge apparatus 100 connected to an ankle brace as further discussed in the description below.

The range limiting system is mentioned shortly in the above description with respect to the tongue 115 and the tongue-stops 170. The range limiting system is now described with respect to the assembled flexion control ankle joint hinge apparatus 100. In the assembled state, the tongue 115 generally pivots above the surface of the distal plate 150 as the proximal plate 105 is rotated with respect to the distal plate 150. The range of movement of the tongue 150 generally follows the path of the conduit 180 on the distal plate 150. By following the general path of the conduit 180, the tongue 115 is limited in its outward motion by coming into contact with the tips 176 of the threaded rods 175 as they sit in a portion of the conduit 180 when in threaded engagement with the tongue-stops 170. With the threaded rods 175 removed or screwed outward to a point so that the tips 176 of the rods 175 do not protrude from the inner portion of the tongue-stop protrusions 170, the tongue 15 generally moves in its widest range of motion. The outer motion of the tongue 15 is limited when its contacts the tongue stops 170. In this orientation, the maximum outward motion of the apparatus 100 is defined. In an opposite extreme, the threaded rods 175 can be screwed inward to their maximum inward position, in which the tips 176 of both the threaded rods 175 contact the tongue 115 at the same time, thereby allowing no motion of the tongue 115 to occur. The threaded rods 175 can be adjusted slightly to still keep the tongue 115 and therefore the proximal plate 105 from rotating with respect to the distal plate 150 and to allow the proximal plate 105 to be oriented in a fixed position with respect to the distal plate 150. As shown in the figures, the threaded rods 175 are oriented in the anterior and posterior directions. By being oriented in the anterior and posterior directions, the apparatus 100 can be adjusted easily without having to remove the brace as described further below. In a typical implementation, the threaded rods 175 can be adjusted with an Allen (or hex) wrench. A typical Allen wrench includes a ninety degree angle so that when a user reaches down the forward portion of the Allen wrench is naturally positioned in the posterior and anterior direction. It is further appreciated that each of the threaded rods 175 can be adjusted and optionally fixed so that the proximal plate 105 moves in a fixed direction or is positioned in a fixed angular position with respect to the distal plate 150.

As described further below with respect to the flexion control ankle joint hinge apparatus 100 connected to an ankle brace, it is typically desired to allow some range of motion depending on the level of therapy of the patient wearing the brace. Therefore, the threaded rods 175 are typically threaded to a setting that allows the tongue 115 to move with some limited motion, thereby allowing the proximal and distal plates 105, 150 to pivot with respect to each other. As can be appreciated by the above description in conjunction with the figures, there is a continuum of positions that are possible by setting the threaded rods 175. It is further appreciated that this range limiting system allows a patient and practitioner to fine tune settings of the apparatus to meet the many different needs of different patients.

FIG. 3 illustrates an embodiment of an ankle brace 200 having an embodiment of flexion control ankle joint hinge apparatus 100 connected to the brace 200. The brace 200 is generally manufactured with dies that are pre-contoured to a particular patient. In another embodiment, the brace 200 can be prefabricated. In general, the brace 200 includes the apparatus 100 as described above. Typically, the brace 200 includes an upper or proximal portion 205 and a lower or distal portion 210. The proximal plate 105 is fixed to the proximal portion 205 of the brace 200 through the brace connection points 108 and screws 190 as described above. The distal plate 150 is fixed to the distal portion 210 of the brace 200 through the brace connection points 160 and screws 190 as also described above. In another implementation, if the patient requires that their ankle remained pointed in one direction, dorsi or plantar, then only one threaded rod can be used, either on the posterior or anterior side.

As described above, the anterior-posterior adjustment of the system provides several advantages. If a practitioner is observing, for example, the gate of a patient wearing the brace 200, the practitioner can make easy adjustments by setting the threaded rods 175 without the patient having to doff the brace 200. Either the practitioner or the patient can easily adjust the level of control, say the dorsi and plantar flexion. As is further appreciated ion the description below, the brace 200 can be custom contoured to the patient then fitted with the apparatus 100 to allow a custom fit for each individual patient.

Furthermore, some patients require free plantar flexion so that the ankle can be bent so that the foot points downward, yet no dorsi flexion, that is, bending the ankle so that the foot points upward. The range limiting system as described above allows this type of setting to be attained by the patient. The range limiting system allows the degree of plantar flexion to be easily set. In addition, the ankle joints can be revered so that there is free dorsi flexion.

A typical metal ankle is squared before plastic is added which can cause premature wearing. If the ankle joint is not square they wear out in the medial and lateral directions, that is, the brace may widen or narrow at the level of the ankle. In a typical implementation, the ankle axis is first located on a negative cast. The cast is drilled at this location and a squaring rod is inserted. The hole is sealed so that there is no subsequent leakage. Then the cast is poured. After the cast has set, then the squaring rod is removed. The resultant cast is a positive cast of the patient's leg with a hole through the ankle axis. The cast is then modified, that is, it is built up in the ankle. A rod that is used to hold square with the ankle is inserted through the hole. At this point, plastic is vacuum formed. Once the plastic has cooled, it is removed from the cast. The plastic is cut all around and the brace is removed. Since the squaring rod is in the way, the hole is cut. The brace is generally removed easily at this point.

The foregoing is considered as illustrative only of the principles of the invention. Further, various modifications may be made of the invention without departing from the scope thereof and it is desired, therefore, that only such limitations shall be placed thereon as are imposed by the prior art and which are set forth in the appended claims.

What is claimed is:

1. An ankle brace flexion joint apparatus, comprising:
   a proximal plate having an upper end and a lower end;
   a distal plate connected to the proximal plate; and
   a range limiting system, comprising:
      a tongue connected to the lower end of the proximal plate;
      two tongue-stops connected to the distal plate at a generally perpendicular orientation, wherein each of the tongue-stops includes a threaded hole through which a threaded rod is connected to the tongue-stops in threaded engagement.

2. The apparatus as claimed in claim 1 further comprising:
   a pin connecting the distal and proximal plates in pivotal arrangement;
   a washer in mechanical engagement with the pin; and
   a clip connected to the pin, the clip preventing the distal and proximal plates from disassembling.

3. The apparatus as claimed in claim 2 wherein the pin comprises:
   a generally cylindrical base;
   a cylindrical stem connected generally perpendicular to a center point of the cylindrical base; and
   a continuous trench on a circumference of the stem adjacent one end of the stem opposite the cylindrical base.

4. The apparatus as claimed in claim 3 wherein the clip is connected to the trench on the stem of the pin.

5. The apparatus as claimed in claim 1 further comprising a conduit located on the distal plate and partially surrounding each of the threaded rods.

6. The apparatus as claimed in claim 1 further comprising ankle brace connection points located on the proximal and distal plates, each ankle brace connection point, comprising a generally circular-shaped base surrounding a hole.

7. The apparatus as claimed in claim 1 wherein the proximal plate further comprises a distal plate connection point having a generally cylindrical depression with a hole located generally in the middle of the depression.

8. The apparatus as claimed in claim 1 wherein the distal plate further comprises a proximal plate connection point having a generally cylindrical depression with a hole located generally in the middle of the depression.

9. An ankle brace system, comprising:
   an ankle brace;
   a flexion joint apparatus connected to the ankle brace, the flexion control apparatus including:
      a proximal plate having an upper end and a lower end;
      a distal plate connected to the proximal plate; and
      a range limiting system, comprising:
         a tongue connected to the second end of the proximal plate;
         two tongue-stops connected to the distal plate at a generally perpendicular orientation, wherein each of the tongue-stops includes a threaded hole through which a threaded rod is connected to the tongue-stops in threaded engagement.

* * * * *